(12) United States Patent
Dumoulin et al.

(10) Patent No.: US 11,789,099 B2
(45) Date of Patent: Oct. 17, 2023

(54) SYSTEM AND METHOD FOR GUIDING AN INVASIVE DEVICE

(71) Applicant: Children's Hospital Medical Center, Cincinnati, OH (US)

(72) Inventors: Charles Lucian Dumoulin, Cincinnati, OH (US); Neil David Johnson, Cincinnati, OH (US); Ronald Gene Pratt, Erlanger, KY (US)

(73) Assignee: Children's Hospital Medical Center, Cincinnati, OH (US)

( * ) Notice: Subject to any disclaimer, the term of this patent is extended or adjusted under 35 U.S.C. 154(b) by 207 days.

(21) Appl. No.: 16/519,314

(22) Filed: Jul. 23, 2019

(65) Prior Publication Data
US 2020/0057123 A1 Feb. 20, 2020

Related U.S. Application Data

(60) Provisional application No. 62/719,768, filed on Aug. 20, 2018.

(51) Int. Cl.
| | | |
|---|---|---|
| *G01R 33/28* | (2006.01) | |
| *A61B 17/34* | (2006.01) | |
| *G01R 33/50* | (2006.01) | |
| *G01R 33/48* | (2006.01) | |
| *A61B 5/055* | (2006.01) | |
| *A61B 90/00* | (2016.01) | |

(52) U.S. Cl.
CPC ........ *G01R 33/285* (2013.01); *A61B 17/3403* (2013.01); *A61B 90/37* (2016.02); *G01R 33/50* (2013.01); *A61B 5/055* (2013.01); *A61B 2090/374* (2016.02); *A61B 2090/3762* (2016.02); *G01R 33/4804* (2013.01)

(58) Field of Classification Search
CPC .......... A61B 17/3403; A61B 2090/364; A61B 2090/374; A61B 2090/3762; A61B 34/20; A61B 5/0036; A61B 5/055; A61B 90/11; A61B 90/13; A61B 90/37; G01R 33/285; G01R 33/4804; G01R 33/50; G01R 33/543
See application file for complete search history.

(56) References Cited

U.S. PATENT DOCUMENTS

| | | | |
|---|---|---|---|
| 5,665,095 A * | 9/1997 | Jacobson | A61B 90/11 604/116 |
| 5,715,836 A | 2/1998 | Kliegis et al. | |
| 5,782,842 A | 7/1998 | Kloess et al. | |
| 6,187,018 B1 | 2/2001 | Sanjay-Gopal et al. | |
| 6,264,665 B1 | 7/2001 | Yu et al. | |
| 6,317,616 B1 | 11/2001 | Glossop | |
| 7,166,113 B2 * | 1/2007 | Arambula | A61B 17/1757 600/417 |
| 8,092,471 B2 | 1/2012 | Momoi et al. | |
| 2006/0184029 A1 | 8/2006 | Haim et al. | |

(Continued)

FOREIGN PATENT DOCUMENTS

WO  WO-2017055990 A1 *  4/2017  ............. A61B 90/11

*Primary Examiner* — Joseph M Santos Rodriguez
*Assistant Examiner* — Maria Christina Talty
(74) *Attorney, Agent, or Firm* — BakerHostetler

(57) ABSTRACT

A system for guiding a medical intervention is disclosed. The system employs a device guide that operates on the surface of a sphere that is centered on a selected target.

16 Claims, 4 Drawing Sheets

(56) References Cited

U.S. PATENT DOCUMENTS

| | | | |
|---|---|---|---|
| 2013/0066192 A1* | 3/2013 | Sarvestani | A61B 17/3403 |
| | | | 600/424 |
| 2013/0267830 A1* | 10/2013 | Ojha | A61B 6/4417 |
| | | | 600/411 |
| 2014/0107473 A1 | 4/2014 | Dumoulin et al. | |
| 2016/0206383 A1* | 7/2016 | Leong | A61B 34/20 |
| 2017/0014200 A1* | 1/2017 | Onuma | A61B 17/3403 |
| 2017/0151027 A1* | 6/2017 | Walker | A61B 34/30 |
| 2018/0185113 A1* | 7/2018 | Gregerson | A61B 6/032 |
| 2018/0200002 A1* | 7/2018 | Kostrzewski | G02C 7/049 |
| 2018/0256262 A1* | 9/2018 | Duindam | A61B 1/2676 |

* cited by examiner

SYSTEM AND METHOD FOR GUIDING AN INVASIVE DEVICE

CROSS-REFERENCE TO RELATED APPLICATIONS

The current application claims priority to U.S. Provisional Application, Ser. No. 62/719,768, filed Aug. 20, 2018, the entire disclosure of which is incorporated by reference.

FIELD OF THE INVENTION

The present disclosure relates generally to invasive medical interventions in a patient undergoing a medical procedure, and more particularly, to a system for guiding invasive devices such as biopsy needles using Magnetic Resonance (MR), Computed Tomography (CT), or other types of images.

BACKGROUND OF THE INVENTION

MR imaging of internal body tissues may be used for numerous medical procedures, including diagnosis and image guidance during surgery. In general terms, MR imaging starts by placing a subject in a relatively uniform, static magnetic field. The static magnetic field causes hydrogen nuclei spins within the subject's body to align with or against the static magnetic field. These two alignments have slightly different energy states and the number of spins in the lower energy (or ground) state is slightly higher than the number of spins in the higher (or excited) state. The nuclear spins precess about the general direction of the magnetic field with a frequency that is proportional to the strength of the static magnetic field. Radio frequency (RF) magnetic field pulses having a frequency that is matched to the precessional frequency of the nuclear spins are then superimposed on the static magnetic field to align the spins in an orientation that has a component that is orthogonal to the static magnetic field, thereby inducing an RF response signal, called the MR echo or MR response signal. The ratio of the number nuclear spins in the aligned verses non-aligned state is defined by the Boltzmann equation:

$$\frac{\text{Number of spins in the excited state}}{\text{Number of spins in the ground state}} = \exp\left(\frac{-(E_{excited} - E_{ground})}{kT}\right) \quad [1]$$

where the ratio of spins in the excited to ground state represents the spin polarization, $E_{excited}$ is the energy level of the excited state, $E_{ground}$ is the energy of the ground state, T is temperature and k is the Boltzmann constant. This ratio defines the overall strength of the observable MR response signal. The MR response signal is further modulated by spin-lattice relaxation times, T1, and spin-spin relaxation times, T2.

It is known that different tissues in the subject produce different MR response signals, and this property can be used to create contrast in an MR image. An RF receiver detects the duration, strength, and source location of the MR response signals, and such data are then processed to generate tomographic or three-dimensional images. Many tissues such as tumors, solid masses, cysts and the like, have unique MR response signals and thus are easily visualized with respect to nearby healthy tissue. Thus, MR images can provide valuable information in medical diagnoses and interventions.

MR imaging can also be used effectively during a medical procedure to assist in locating and guiding medical instruments. For example, a medical procedure can be performed on a patient using medical instruments while the patient is in an MRI scanner. The medical instruments may be inserted into the patient or they may be used externally but still have a therapeutic or diagnostic effect. For instance, the medical instrument can be an ultrasonic device, which is disposed outside a patient's body and focuses ultrasonic energy to ablate or necrose tissue or other material on or within the patient's body. The MM scanner preferably produces images at a high rate so that the location of the instrument (or the focus of its effects) relative to the patient may be monitored in real-time (or substantially in real-time). The MM scanner can be used for both imaging the targeted body tissue and locating the instrument, such that the tissue image and the overlaid instrument image can help track an absolute location of the instrument as well as its location relative to the patient's body tissue.

Although MR imaging provides excellent visualization of interventional targets such as tumors, cysts, and other masses, the proximity of the magnet to the patient can make many interventions difficult or impossible. In many interventions the device is too long, or requires the immediate presence of one or more interventionist to operate. Furthermore, the image quality afforded by the rapid imaging used to follow an invasive device in real-time may be insufficient to visualize the targeted body tissue.

Computed Tomography employs an X-ray source and X-ray detector that is rotated around the patient. The X-rays passing through the patient from a variety of directions are detected and measures of X-ray intensity are sent to a reconstruction algorithm which produces a cross-sectional image whose information content reflects the X-ray attenuation properties of tissue. In general, CT gantries are thinner than MR magnets and from a geometric point of view are easier to use for image-guided interventions, but even so, the proximity of the gantry can make some interventions difficult or impossible.

For interventions relying on MR or CT imaging it can be advantageous to remove the patient from the magnet or gantry so that the intervention can be performed in a relatively unobstructed environment. If the acquired MR or CT images are to be used for guidance in the intervention, it is important that the geometric space of the imaging system be registered with the geometric space of the interventional environment. It is convenient to define the isocenter of an MR magnet or CT gantry as the center (or zero) of the imaging space since that is where the images are acquired.

Traditionally, patient placement at the magnet or gantry isocenter is accomplished with a landmarking laser cross-hair that is positioned a known distance from the imaging isocenter in the direction of the patient table motion. Before insertion into the imaging gantry the patient is moved under the landmarking laser until the laser cross-hair falls on, or near, the region of anatomy of interest. The operator then declares a landmark, typically by depressing a landmark button, and then advances the patient into the gantry using a second button, switch or lever. The imaging system is designed to bring the anatomy identified by the landmark button push to the imaging gantry center, typically with millimeter accuracy.

Since modern MR and CT systems can acquire multiple image slices or even a full volume of data, there is not a need for the landmarking procedure to be accurate with respect to aligning pathology with the imaging system's isocenter.

Once images are acquired, the location of any tissue of interest can be determined in three dimensions as long as it is within the imaging volume of the scanner. It is important to note, however that this location is with respect to the imaging system's isocenter. Thus, if the patient is moved to a new location with a new coordinate system, it is important to accurately register the patient with the new coordinate system so that the tissue of interest can be found using the imaging data in the new coordinate system. In view of the foregoing, it may be understood that the ability to accurately locate a target inside the body in one coordinate space using images acquired in a different coordinate space may be desirable and advantageous under some circumstances.

SUMMARY

Embodiments of the present disclosure provide a device guide system that may be useful in Magnetic Resonance Imaging (MRI), Computed Tomography (CT), Gamma Camera, Positron Emission Tomography (PET), and Radiation Therapy (RT) systems. In one embodiment, an operator first selects an anatomic feature of interest on the patient and landmarks the imaging or RT system on that feature. The anatomic feature of interest may be a physical feature of the patient or a physical mark made on the skin of the patient by the operator. In general, the anatomic feature of interest is selected to be close to an interventional target inside the patient. Once the landmark has been declared, the operator moves the patient to the isocenter of the imaging system so that the landmarked portion of the patient is at the isocenter of the imaging system. It should be noted that in such an embodiment the operator can be a natural person, or an artificial intelligence system configured to act like a natural person within the extent of patient landmarking process disclosed here. Once the patient is at the imaging system isocenter, images are acquired and presented to the operator. The operator then extracts location information of the interventional target from the images. This location information can take the form of the X, Y and Z address of the target relative to the imaging system's isocenter. Note that because the landmarked portion of the patient is at the isocenter, the X, Y and Z address of the target is also relative to the patient's landmark. The operator then removes the patient from the imaging gantry and places them under a guidance frame supporting a fixed positioning laser and a movable positioning laser. The anatomic feature of interest used for image landmarking is placed under the fixed positioning laser, which defines the center of the guidance frame's coordinate system. The movable positioning laser is then moved to a point that is a distance R from the X, Y, and Z coordinates of the target of interest in the guidance frame's coordinate system, where movable positioning laser beam is directed towards the X, Y and Z coordinates of the target of interest with respect to the guidance frame's coordinate system. In the current embodiment the frame is designed to allow the movable positioning laser to move over an imaginary partial spherical surface having a radius R, and centered at the X, Y and Z coordinates of the target of interest, where the movable positioning laser continues to be pointed to the X, Y and Z coordinates of the target of interest while moving about the spherical reference frame. The movable positioning laser is configured on the movable portion of the guidance frame such that the laser beam always points through the center of the imaginary sphere. Consequently, when the sphere is centered on the interventional target, the laser always points to the target regardless of where on the spherical surface the laser is located. The operator selects a path to the target by moving the movable positioning laser to point to any desired entry point on the patient's skin. Inserting a needle at the point where the laser falls on the skin, and aligning the needle with the laser beam allows the operator to directly access the target.

Note that for the purpose of this disclosure the terms "sphere", and "spherical surface" do not necessarily refer to a physical object. Rather, the terms are used to mean a region of space described by the mathematical equation for a sphere. In Cartesian coordinates, this equation can be given as:

$$(X-X_0)^2+(Y-Y_0)^2+(Z-Z_0)^2=R^2 \qquad [2]$$

where $X_0$, $Y_0$, and $Z_0$ are the coordinates of the center of the sphere and R is the radius of the sphere.

In an alternate embodiment of the present disclosure, the operator acquires two sets of coordinates from the images. The first set of coordinates is the location of the interventional target and the second set is the location of a waypoint for the interventional device as it is inserted in the patient on its way to the target. This waypoint can be on the patient's skin, or it can be a point deeper in the patient. The two points define a line in space, which permits the angles, $\Theta$ and $\Phi$, of the laser guide on the sphere's surface to be computed. In this alternate embodiment, the X, Y, and Z location of the target, and the rotational angles $\Theta$ and $\Phi$ are used to align the laser.

In selected embodiments of the present disclosure the positioning of one or more positional attributes (i.e. X, Y, Z, $\Theta$ and $\Phi$ in a standard coordinate space, such as a spherical coordinate space) of the guidance frame are under the control of a computer-controlled stepper motor. In other selected embodiments one or more positional attributes are manipulated by hand.

In yet another embodiment, the values of the positional attributes of the guidance frame can be detected and used to control a computer display. For example, if a full three-dimensional image of the interventional target and its surroundings has been acquired, then the guidance frame can be manipulated and the computer display can be updated in real time to show images of the anatomy that are in alignment with the laser.

In another embodiment according to the current disclosure, a system for guiding an interventional device to a selected target within a body is provided. Such a system includes: a device guide; a first adjustment assembly retaining the device guide, where the first adjustment assembly allows adjustment of the position and orientation of the device guide along the surface of a mathematical sphere having a center C and a radius R, and where the first adjustment assembly retains the device guide so that the device guide is directed towards the center C of the mathematical sphere at least during adjustment; and a second adjustment assembly supporting the spherical guide assembly, where the second adjustment assembly allows adjustment of the position of the spherical guide assembly with respect to a patient in at least two linear dimensions (e.g, X and Y, or X and Z, or Y and Z or X, Y and Z). In a more detailed embodiment, the system further includes a guide frame configured to support the second adjustment assembly approximate the patient. In yet a further detailed embodiment, the system further includes a landmarking assembly configured to register the position of the patient with respect to a coordinate system of the guide frame. In yet a further detailed embodiment, the landmarking assembly includes a positional laser mounted to the guide frame. Alternatively, or in addition, the system further includes a computer control configured to receive or compute coordinates of an interventional target within the patient with respect to a landmark, receive or compute a position of the landmark with respect to the guide frame's coordinate system, and to control movement of the second adjustment assembly so that the center C of the mathematical sphere corresponds to the interventional target.

In a detailed embodiment, the device guide may include a positional laser emitting a laser beam, or the device guide may include a projector projecting an image (such as a cross-hair symbol, for example). In a more detailed embodiment, the device guide may further include an intervention device, where the laser beam or image projection of the device guide is coaxial or parallel with an intervention direction of the intervention device.

In an alternate detailed embodiment, the first adjustment assembly includes: an arc having the center C retaining the device guide so that the device guide is directed at center C; a bearing retaining the arc for translational movement of the arc about center C; and a pivot retaining the bearing for rotational movement of the arc on a diametrical axis passing through center C. In a further detailed embodiment, the arc retains two or more positional lasers emitting laser beams directed at center C.

In an alternate detailed embodiment, the first adjustment assembly allows adjustment of the position and orientation of the device guide along only a portion of the mathematical sphere less than the entire mathematical sphere. In yet a further detailed embodiment, the portion of the mathematical sphere is positioned over the patient. Alternatively, or in addition, the mathematical sphere is a physical or an imaginary sphere.

In an alternate detailed embodiment, the first and second adjustment assemblies are integrated into an adjustment system allowing adjustment in X, Y, Z, $\Theta$, and $\Phi$ coordinates. In a further detailed embodiment, the integrated adjustment system comprises a multi-axis articulated robotic arm and the system further comprises a landmarking assembly configured to register the position of the patient with respect to a coordinate system of the robotic arm.

In another embodiment according to the current disclosure, a system for guiding an interventional device to a selected target within a body is provided. Such an embodiment includes: an imaging system configured to compute and provide coordinates of a target within a patient with respect to a first coordinate system and with respect to a landmark on the patient; a registration assembly configured to register the landmark with respect to a second coordinate system; a device guide; a first adjustment assembly retaining the device guide, where the first adjustment assembly allows adjustment of the position and orientation of the device guide along the surface of a mathematical sphere having a center C and a radius R, and where the first adjustment assembly retains the device guide so that the device guide is directed towards the center C of the mathematical sphere at least during adjustment; and a second adjustment assembly supporting the spherical guide assembly, where the second adjustment assembly allows adjustment of the position of the spherical guide assembly in three dimensions in the second coordinate system so that center C is located at the coordinates of the target with respect to the landmark.

In another embodiment according to the current disclosure a method for guiding an interventional device to a selected target within a patient is provided. Such method includes the following steps: (A) providing (i) a device guide, (ii) a first adjustment assembly retaining the device guide, where the first adjustment assembly allows adjustment of the position and orientation of the device guide along the surface of a mathematical sphere having a center C and a radius R, and where the first adjustment assembly retains the device guide so that the device guide is directed towards the center C of the mathematical sphere at least during adjustment, (iii) a second adjustment assembly supporting the spherical guide assembly, where the second adjustment assembly allows adjustment of the position of the spherical guide assembly with respect to a patient in three dimensions, and (iv) a guide frame retaining the second adjustment assembly; (B) receiving or computing coordinates of an interventional target within the patient with respect to a landmark on the patient; (C) receiving or computing a position of the landmark with respect to the guide frame's coordinate system; (D) actuating the second adjustment assembly so that the center C of the mathematical sphere corresponds to the interventional target; and (E) actuating the first adjustment assembly to a desired interventional position and orientation of the device guide along the mathematical sphere with respect interventional target.

In a more detailed embodiment, the step of receiving or computing coordinates of an interventional target within the patient with respect to a landmark on the patient is performed utilizing a Magnetic Resonance Imaging system, a Computed Tomography system, a Positron Emission Tomography system, a Gamma Camera system, or an ultrasound system.

The inventions will now be described in more detail with reference to exemplary embodiments thereof as shown in the accompanying drawings. While the inventions are described below with reference to exemplary embodiments, it should be understood that the inventions are not limited thereto. Those of ordinary skill in the art having access to the teachings herein will recognize additional implementations, modifications, and embodiments, as well as other fields of use, which are within the scope of the inventions as described herein, and with respect to which the inventions may be of significant utility.

BRIEF DESCRIPTION OF THE DRAWINGS

In order to facilitate a fuller understanding of the exemplary embodiments, reference is now made to the accompanying drawings, in which like elements are referenced with like numerals. These drawings should not be construed as limiting the inventions, but are intended to be exemplary only.

FIG. 4b is a side view with respect to FIG. 4a.

DETAILED DESCRIPTION

Embodiments of the present disclosure provide systems and methods to guide the placement of an interventional device to a selected target within a patient.

Figure 1:
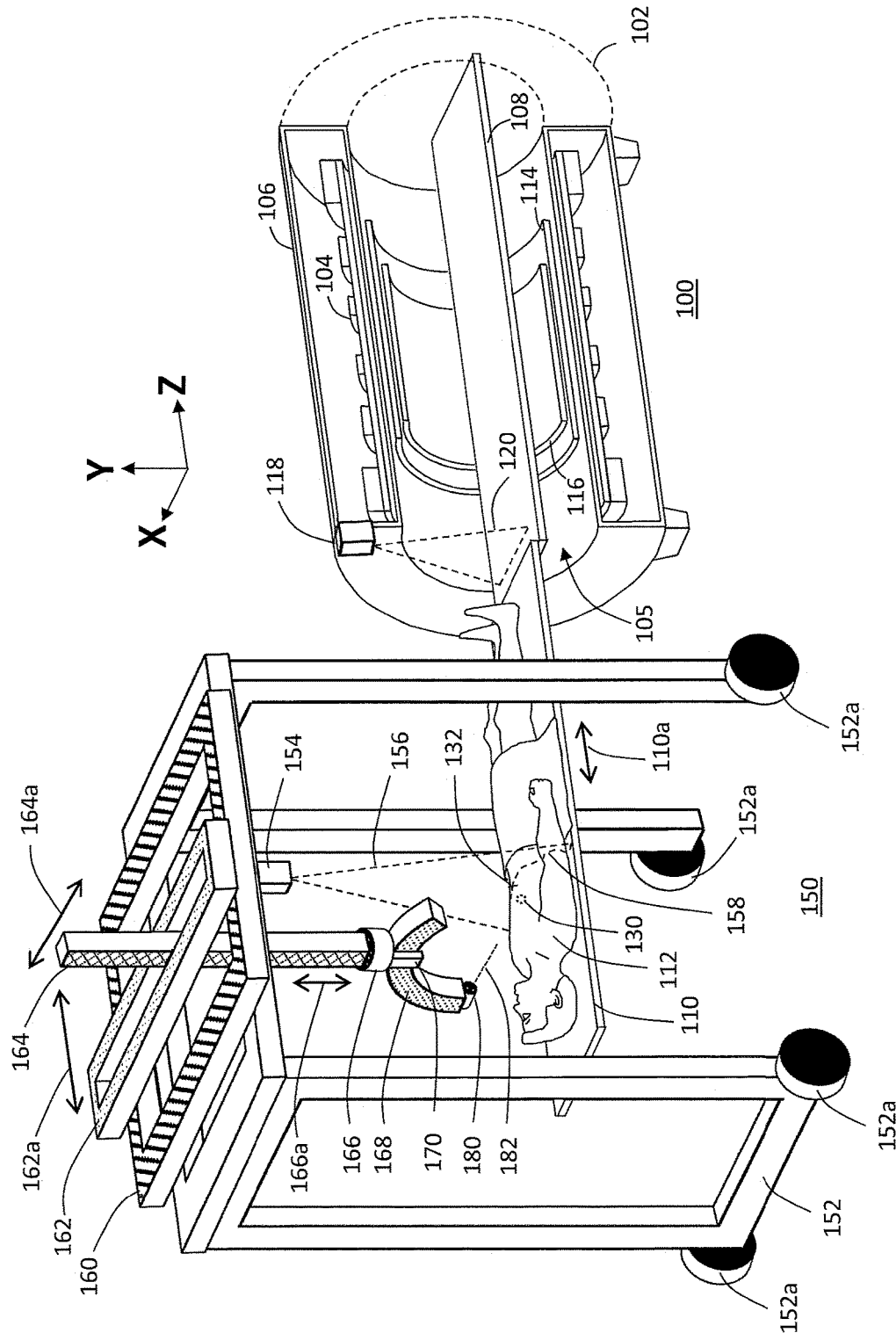
FIG. 1 shows an exemplary MRI system and exemplary laser guidance frame for which the techniques for the use of the current disclosure may be implemented.

FIG. 1 shows an exemplary MM system 100 and an exemplary guidance frame 150 in or for which techniques of laser interventional device guidance using MR imaging data in accordance with the present disclosure may be implemented. The illustrated MM system 100 comprises an Mill scanner 102. Since the components and operation of the Mill scanner are well-known in the art, only some basic components helpful in the understanding of the system 100 and its operation will be described herein.

The MM scanner 102 typically comprises a cylindrical superconducting magnet 104, which generates a static magnetic field within a bore 105 of the superconducting magnet 104. The superconducting magnet 104 generates a substantially homogeneous magnetic field within an imaging region inside the magnet bore 105. The superconducting magnet 104 may be enclosed in a magnet housing 106. A support table 108, upon which a patient table 110 lies, is disposed within the magnet bore 105. Patient table 110 is configured to slide into and out of Mill scanner 102. A patient 112 is positioned on top of patient table 110 in a supine, prone, or other orientation. Patient table 110 moves in a linear direction 110a that is parallel to magnet bore 105. One intent of the present disclosure is to identify a desired region of interest within patient 112 and position it within the imaging region of the Mill scanner 102 which is typically the center of the superconducting magnet 104.

A set of cylindrical magnetic field gradient coils 114 may also be provided within the magnet bore 105. The gradient coils 114 also surround the patient 112. The gradient coils 114 can generate magnetic field gradients of predetermined magnitudes, at predetermined times, and in three mutually orthogonal directions within the magnet bore 105. With the field gradients, different spatial locations can be associated with different precession frequencies, thereby giving an MR image its spatial resolution. An RF transmitter coil 116 surrounds the imaging region. The RF transmitter coil 116 emits RF energy in the form of a rotating magnetic field into the imaging region.

The RF transmitter coil 116 can also receive MR response signals emitted from the region of interest. The MR response signals are amplified, conditioned and digitized into raw data using an image processing system (not shown), as is known by those of ordinary skill in the art. The image processing system further processes the raw data using known computational methods, including fast Fourier transform (FFT), into an array of image data. The image data may then be displayed on a monitor, such as a computer CRT, LCD display or other suitable display.

To make MR images of the anatomy of interest in patient 112 it is desired to put the anatomy of interest substantially in the center of superconducting magnet 104, gradient coils 114, and RF transmitter coil 116. In the current embodiment this is accomplished using a landmarking positioning laser 118 that creates a visual landmarking laser beam 120. Landmarking laser beam 120 substantially appears as a line on the surface of patient 112 when patient 112 is positioned under it. Landmarking laser 118 can be mounted in the ceiling above patient 112, on MRI scanner 102, or placed in any known location near patient 112. The system operator moves patient 112 towards magnet bore 105 until the desired patient anatomy is appropriately positioned under landmarking laser beam 120. The desired patient anatomy can be identified by a superficial feature 132 which can be a naturally occurring anatomic feature, a marking made by the operator or other medical staff, or an object of interest such as an item of clothing or MR imaging coil. Once the operator is satisfied that superficial feature 132 is properly aligned with landmarking laser beam 120, the operator declares a landmark (such as through computer controls associated with the MRI scanner) and invokes the imaging system's control electronics to pull patient table 110 until superficial feature 132 is located at the center of magnet 104 (or to some other predetermined position with respect to the magnet). The operator can then proceed to scan the patient.

Once the patient has been scanned, the images are examined and the location of an interventional target 130 is identified. This location is relative to the center of the coordinate system of the magnet and is conveniently expressed in a three-dimensional Cartesian system as an X, Y, Z address. If desired, additional locations of interest can be identified for further use.

The operator then moves the patient out of Mill scanner 102 and under guidance frame 150. Guidance frame 150 is comprised of a support structure 152. In FIG. 1, support structure 152 is configured to roll on wheels 152a and designed to straddle MRI scanner 102's patient bed 110 after it has been moved out of the scanner 102. Alternate embodiments of guidance frame 150 include support structure 152 suspended from the ceiling and support structure 152 placed substantially to the side of patient 112. Once patient 112 is appropriately positioned with respect to guidance frame 150, a guidance alignment positioning laser 154 is turned on. Guidance alignment laser 154 creates a laser beam 156 that is made to fall on patient 112 to create a reference laser line 158. Patient 112 is moved along linear direction 110a until superficial feature 132 is aligned with reference laser line 158.

Note that the location of laser line 158 defines the Z=0 location of guidance frame 150. In the present embodiment the X=0 and Y=0 are known because the relative locations of guidance frame 150 and MM scanner 102 are fixed by the geometric construction of MRI scanner 102 and guidance frame 150. In alternate embodiments additional alignment lasers used to register patient 112 in the X and Y directions are possible.

The primary purpose of support structure 152 is to provide a stable foundation for a three-dimensional guidance laser positioning stage. The three-dimensional stage in this embodiment is comprised of a Z-axis positioner guide panel 160 supporting for movement an X-axis guide bar 162 that in turn supports for movement a Y-axis guide bar 164. Z-axis positioner guide panel 160 moves X-axis positioner guide bar 162 along a Z linear path 162a that is substantially parallel to the Z axis of MRI scanner 102. X-axis positioner guide bar 162 moves Y-axis positioner guide bar 164 along an X linear path 164a that is substantially parallel to the X axis of MRI scanner 102. Y-axis positioner guide bar 164 moves a pivot mount 166 along a Y linear path 166a that is substantially parallel to the Y axis of Mill scanner 102.

Pivot mount 166 attaches at the base of Y-axis positioner guide bar 164 and is configured to rotate around the Y-axis. In one embodiment of the present disclosure pivot mount 166 can rotate 360 degrees or more. The pivot mount 166 includes a guide bearing 170 extending therefrom in which an arcuate guide bar 168 with a selected radius, R, is received and adapted to slide there-within.

A positioning guide laser 180 is affixed to arcuate bar 168 and positioned in a way that it creates a guide laser beam 182 that passes substantially through the center of curvature of arcuate bar 168. Thus, as the arcuate bar 168 is pivoted/rotated around the Y-axis and/or is slid through the guide bearing 170, guide laser beam 182 always intersects the center of curvature of arc 168. The combination of the pivot mount 166, arcuate bar 168 and guide bearing 170 provide a spherical guide assembly adapted to guide adjustment of the positioning guide laser 180 along the surface of an imaginary (or physical in certain embodiments) sphere centered at the interventional target 130 and having a radius R.

When using the current embodiment the operator obtains the X, Y and Z coordinates of the interventional target 130 with respect to the MR system 100, registers patient 112 in guidance frame 150, and then, knowing the X, Y and Z position of the interventional target 130 with respect to the registered position, moves guide bar 162 within Z-axis positioner guide panel to position with respect to the Z-axis 162a, moves guide bar 164 along the X-axis 164a within X-axis positioner guide bar 162 to position with respect to the X-axis 164a, and also moves guide bar 164 along the Y-axis within the guide bar 162 to position with respect to the Y-axis, so that the center of curvature of arcuate bar 168 is placed at the X, Y and Z position of interventional target 130 with respect to the guidance frame 150. The combination of the Z-axis positional guide panel 160, X-axis guide bar 162 and Y-axis guide bar 164 provide an example of a three-dimensional adjustment assembly that allows the user to either manually or automatically move the positioning laser 180 in three-dimensions (X, Y and Z) so that the laser beam 182 is directed to the registered position of interventional target 130. Once patient 112 and three-dimensional adjustment assembly is properly positioned, the three-dimensional adjustment assembly can be locked into place, laser 180 can be turned on, and then the user can manipulate, either manually or automatically, the position of the laser 180 along an imaginary spherical surface centered on the position of the interventional target 130 (by rotating arcuate bar 168 and guide bearing 170 within pivot mount 166 and by sliding arcuate bar within guide bearing 170) to find a suitable entry point and direction of intervention with respect to the patient 112. Wherever guide laser beam 182 hits the surface of patient 112 is a possible entry point for the insertion of an interventional device such as a needle. Since guide laser beam 182 always intersects interventional target 130 the interventional device simply needs to be aligned with the laser beam 182 to be properly aligned for a trajectory that will take the device to the target. If the entry point is deemed to be not suitable, then the arcuate bar 168 can be pivoted and/or slid to a new position.

Figure 2:
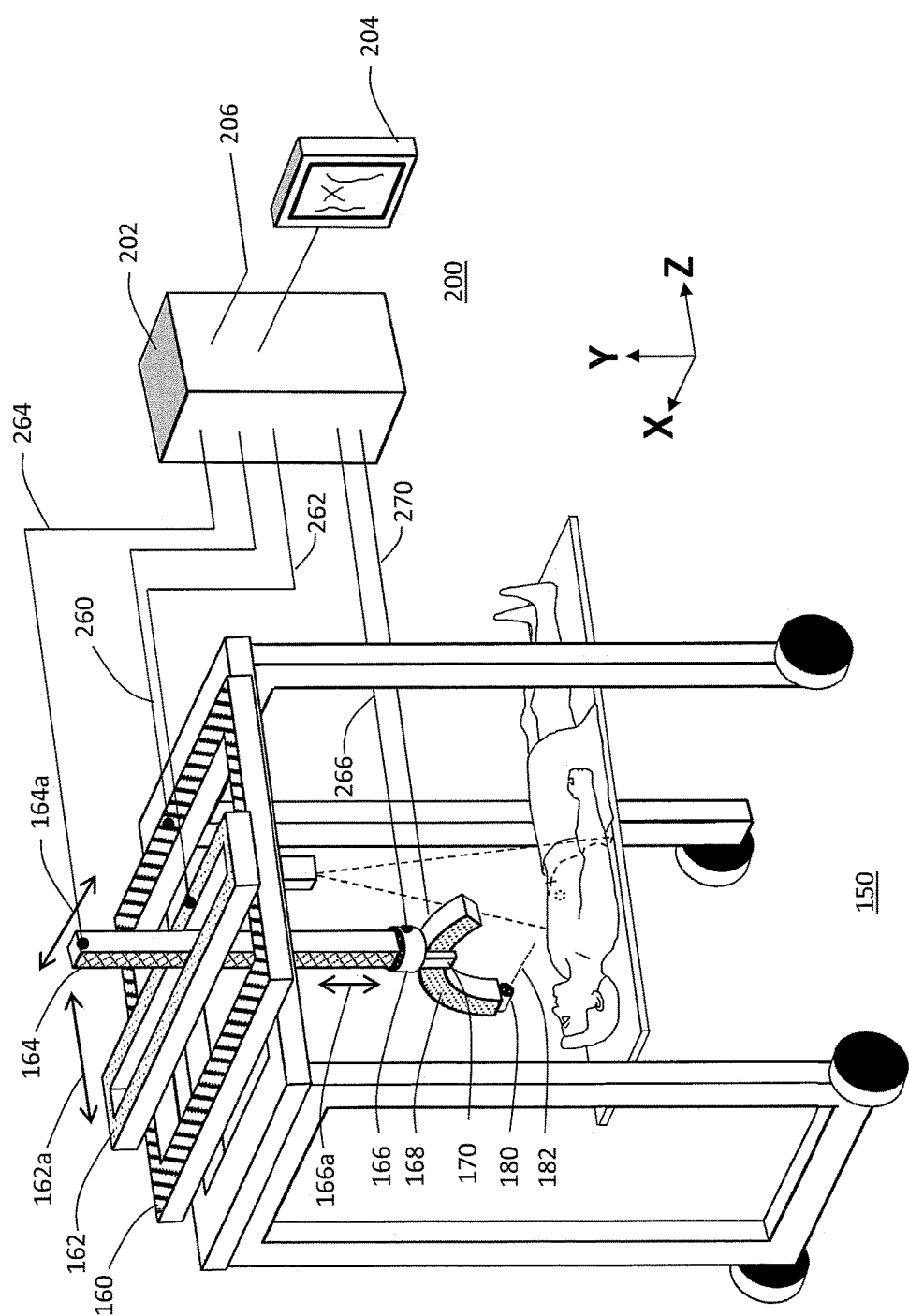
FIG. 2 another exemplary laser guide system and controller configured to display anatomic images that are aligned with the laser guide.

FIG. 2 shows an alternate embodiment and use of the present disclosure. In this embodiment a control system 200 comprised of a control unit 202, display unit 204, and control input 206 is integrated with guidance frame 150. Control unit 202 is attached to Z-axis positioner guide panel 160 via a Z-axis interface line 260. Z-axis interface line 260 can be configured to control a stepper motor or actuator that moves guide bar 162 within Z-axis positioner guide panel 160. If desired it can also include the ability to relay position information to control unit 202. Likewise, X-axis guide bar 162 is attached to control unit 202 via X-axis interface line 262, and Y-axis positioner guide bar 164 is attached to control unit 202 via Y-axis interface line 264. In a similar fashion, pivot mount 166 can be attached to control unit 202 via pivot interface line 266, and arc slide guide bearing 170 can be attached to control unit 202 via slide interface line 270. The purpose of attaching these control and sense lines is to enable computer control of the X, Y, Z, Θ, and Φ, location and orientation of guide laser 180, and computer monitoring of the position of laser 180. In one embodiment control system 200 is used to automatically align guide laser 180 using target and trajectory information acquired from MR images. In another embodiment, control system 200 is used to position pivot mount 166 over patient 112, and the operator is allowed to freely pivot and slide arcuate guide bar 168. In yet another embodiment of the present disclosure guide laser 180 is moved manually by pivoting and sliding the arcuate guide bar 168. The location and orientation of guide laser 180 is relayed to control unit 202 which then displays selected MRI images extracted from the previously acquired MR image data that show the anatomy along the path of guide laser beam 182.

Figure 3:
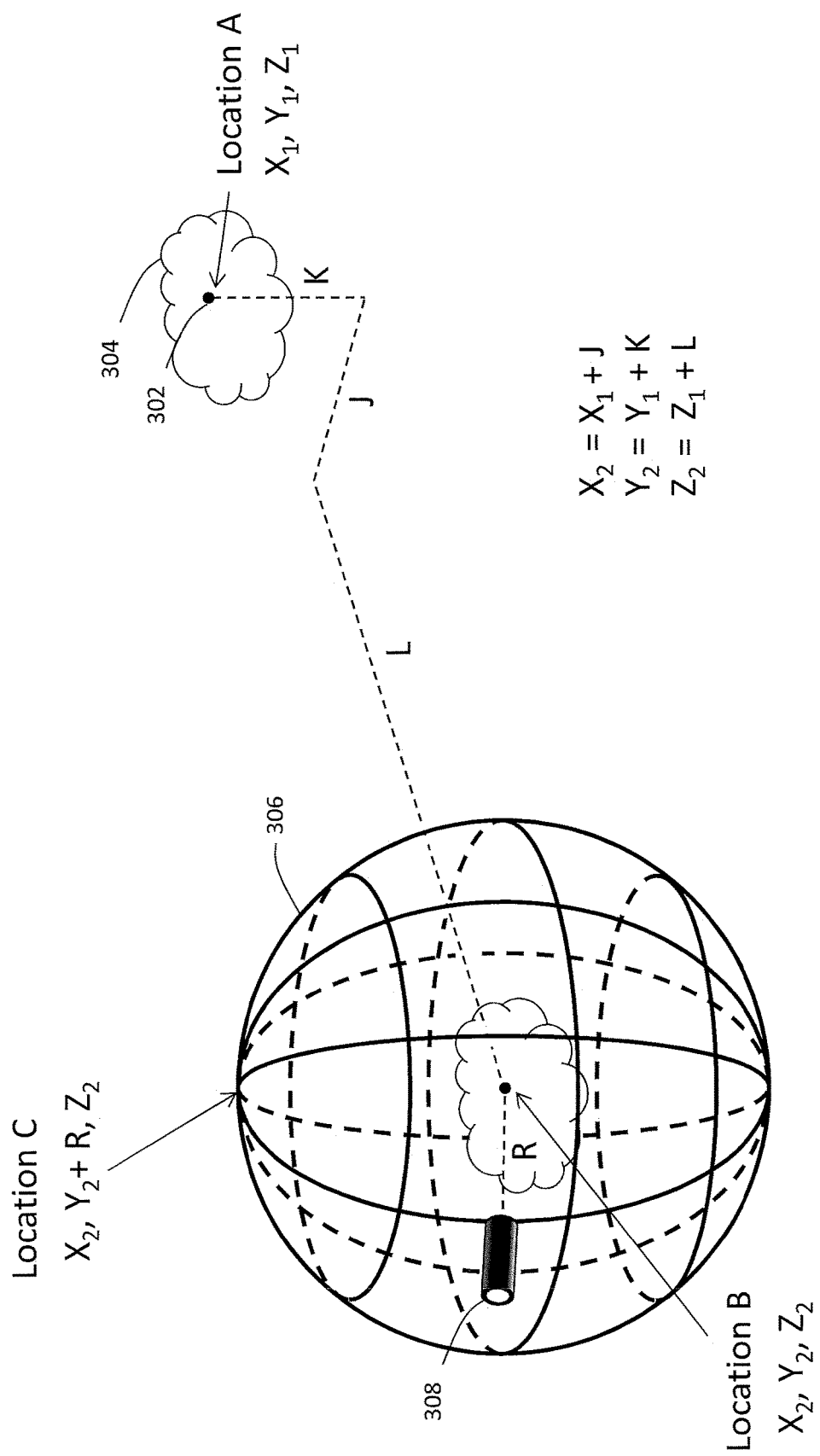
FIG. 3 shows the geometric relationship between the imaging and guide coordinate systems in accordance with an embodiment of the present invention.

FIG. 3 shows the mathematical relationship at the heart of the present disclosure. In this figure an object 302 is found at Location A using an imaging or other locating system. Note that the object can be embedded inside an opaque body 304 and not be readily accessible. Body 304 and object 302 are then translated from Location A to a new location such that object 302 is now at Location B. In the figure, this translation is shown in three orthogonal steps (translational steps K, J and L), but in general any translation and change in orientation is possible. Knowing Location A and the displacement of body 304, it is possible to determine Location B, even without having immediate access to that point in space. Location B can be defined to be the center of a sphere 306 having a radius R. Unlike the center of the sphere, the surface of the sphere can be made accessible if R is bigger than body 304 containing the object. A laser 308 is placed on the surface of sphere 306 and orientated to be orthogonal to the surface of the sphere. Consequently, wherever the laser is moved on the surface of the sphere, its beam intersects the center of the sphere which is position at Location B. Location C of FIG. 3 can correspond to one possible position of the pivot mount/guide bearing 166/170 of FIGS. 1 and 2. Further, with respect to FIG. 3, in the implementation shown in FIGS. 1 and 2, the dimensions of J, K and L would be 0, 0 and the distance from the isocenter of the imaging gantry to the isocenter of the guidance frame 150. Note that a needle holder/guide orientated orthogonal to the surface of the sphere (in place of the laser 308 or incorporating the laser) is also within the scope and spirit of the current disclosure; for example the laser 380 can be incorporated into an instrument guide where the positioning beam of the laser 380 is coaxial (or parallel) to the intervention path of the instrument being guided by the instrument guide.

Figure 4B:
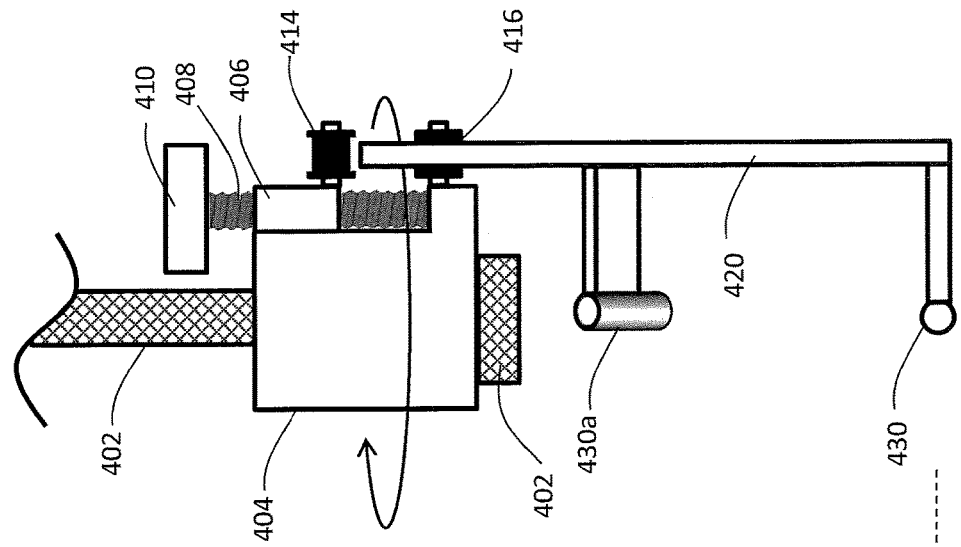
Figure 4A:
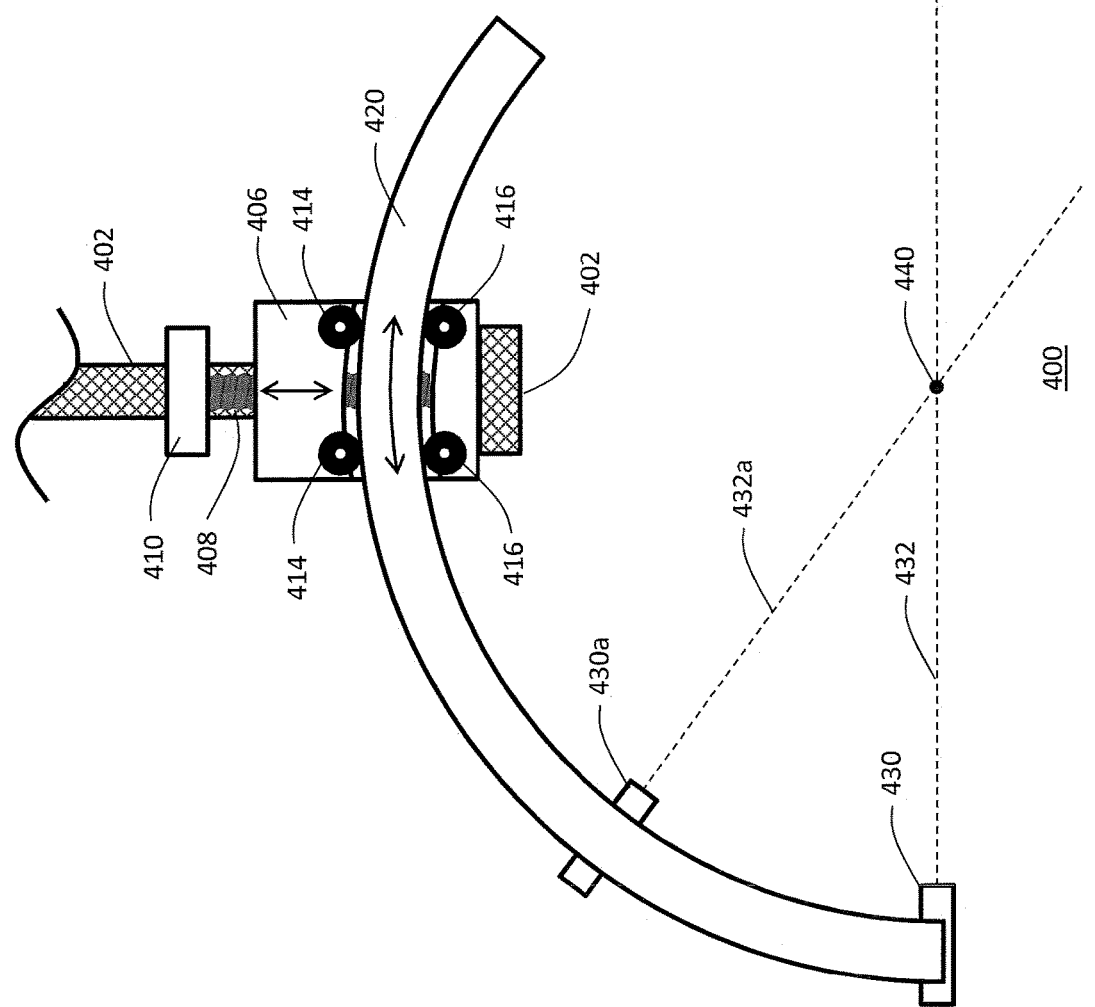
FIG. 4a is a front view of a spherical surface guide assembly according to an embodiment using two positioning lasers to be manipulated on the surface of a sphere whose center has been placed at a desired location in accordance with an embodiment of the present invention.

FIGS. 4a and 4b provide a detailed view of one embodiment 400 of an exemplary spherical guide assembly adapted to guide adjustment of the positioning guide laser 430/430a along the surface of an imaginary sphere centered at the interventional target 440 and having a radius R. In this embodiment, a support shaft 402 is attached to a positioning system (not shown), such as a three-dimensional adjustment assembly described above. At the end of support shaft 402 is a pivot block 404 that is configured to rotate around support shaft 402. On the face of pivot block 404 is a slide block 406 that can be moved in response to the turning of a threaded rod 408 which is manipulated with knob 410. Pivot block 404 has two lower casters 416 that can freely roll. Slide block 406 has two upper casters 414 that also can freely roll. In between lower casters 416 and upper casters 414 an arc 420 with a radius R is placed. Knob 410 is turned so that arc 420 is captured between lower casters 416 and upper casters 414. A laser 430 is attached to arc 420 in such a way that it produces a laser beam 432 that passes through the geometric center 440 of arc 420.

If desired, a second laser 430a creating a second laser beam 432a can be added to arc 420. The purpose of the second laser is to give the operator wider latitude in positioning the arc over the patient. If arc 420 covers 180 or more degrees it is possible in theory to shine laser beam 432 anywhere on the surface of the patient facing the arc, but in practice some orientations may not be possible. In particular, if the arc is slid into position to provide a laser beam 432 that is substantially parallel with support shaft 402, the far end of arc 420 will be in a position that could be in conflict with the patient. By shortening arc 420 to 120 degrees and adding second laser 430*a* it is possible to select one or the other laser without risking the far end of the arc hitting the patient. As will be appreciated by those of ordinary skill, more than two positioning lasers 430/430*a* may be utilized in a similar fashion.

Additional embodiments and modifications included in the spirit of this disclosure include:

A) The use of other imaging technologies such as ultrasound, X-ray, and optical tomography capable of revealing interventional targets.

B) The use of non-imaging technologies such as radiofrequency ID transponders to identify interventional targets.

C) The use of a multi-axis articulated robotic arm to provide the functionality of the three-dimensional adjustment assembly, the spherical guide assembly or a combination of the three-dimensional adjustment assembly and the spherical guide assembly described above. In such an embodiment, the guide frame may be the chassis of the robot supporting the robotic arm.

D) The disposition of the guidance frame in a room different than the one containing the imaging system.

E) The use of more than one laser on the arc to provide enhanced operational flexibility.

F) Replacement or supplementation of the guide laser with an apparatus that physically guides a device to the target.

G) Replacement or supplementation of the guide laser with an apparatus that projects an image such as a bull's eye target or cross hair on the patient.

H) The use of a range sensor and/or indicator to show the depth of the device as it is inserted into the patient.

I) The determination of the distance between the laser or device guide and the patient's skin to determine the remaining distance from the skin to the target.

J) The use of markers affixed to the patient or table to register the imaging frame of reference with the frame of reference of the guidance frame.

K) The incorporation of slide rails, expansion joints, and hinges to permit the guidance frame to fit into tight spaces for transport and storage.

L) The use of the guidance system for biopsies, laser ablations, cryoablations, laparoscopy, High-Intensity Focused Ultrasound (HIFUtreatments, small surgical incisions, large surgical incisions, and other invasive and non-invasive procedures.

Salient aspects of the current disclosure include:

A) The guidance system does not have to be tightly integrated with the imaging system. If the guidance and imaging systems are properly aligned with respect to each other, the only data that needs to be carried from the imaging system to the guidance system are the X, Y, and Z coordinates of the target.

B) The guidance system can work with computer-controlled actuators or with manual motions, or with a combination of computer-controlled actuators and manual motions.

C) A single guidance system can be configured to work with a variety of MR, CT and X-ray system beds.

While the foregoing description includes many details and specificities, it is to be understood that these have been included for purposes of explanation only, and are not to be interpreted as limitations of the claimed inventions. It will be apparent to those skilled in the art that other modifications to the embodiments described above can be made without departing from the spirit and scope of the inventions as claimed. Accordingly, such modifications are considered within the scope of the disclosure as intended to be encompassed by the following claims and their legal equivalents.

What is claimed is:

1. A system for guiding an interventional device to a selected target within a patient, comprising:
   a device guide;
   a spherical guide assembly retaining the device guide, the spherical guide assembly including a pivot mount supporting a guide bar on which the device guide is retained, the pivot mount allowing adjustment of a position and an orientation of the device guide along the a surface of a mathematical sphere having a center C and a radius R, the spherical guide assembly retaining the device guide so that the device guide is directed towards the center C of the mathematical sphere at least during adjustment; and
   an adjustment assembly supporting the spherical guide assembly, the adjustment assembly allowing adjustment of the position of the spherical guide assembly with respect to the patient in at least two linear dimensions;
   wherein the pivot mount is capable of rotating 360 degrees around a longitudinal axis defined by the guide bar.

2. The system of claim 1, further comprising a guide frame configured to support the adjustment assembly approximate the patient.

3. The system of claim 2, further comprising a landmarking assembly configured to register a position of the patient with respect to a coordinate system of the guide frame.

4. The system of claim 3, wherein the landmarking assembly includes a positional laser mounted to the guide frame.

5. The system of claim 3, further comprising a computer control configured to receive or compute coordinates of the selected target within the patient with respect to a landmark, receive or compute a position of the landmark with respect to the guide frame's coordinate system, and to control movement of the adjustment assembly so that the center C of the mathematical sphere corresponds to the selected target.

6. The system of claim 1, wherein the device guide includes a positional laser emitting a laser beam.

7. The system of claim 6, wherein the device guide further includes an intervention device wherein the laser beam of the device guide is coaxial or parallel with an intervention direction of the intervention device.

8. The system of claim 1, wherein the spherical guide assembly comprises:
   an arc having the center C retaining the device guide so that the device guide is directed at center C; and
   wherein the pivot mount comprises:
   a bearing retaining the arc for translational movement of the arc about center C; and
   a pivot retaining the bearing for rotational movement of the arc on a diametrical axis passing through center C.

9. The system of claim 8, wherein the arc retains two or more positional lasers emitting laser beams directed at center C.

10. The system of claim 1, wherein the spherical guide assembly allows adjustment of the position and orientation of the device guide along only a portion of the mathematical sphere less than the entire mathematical sphere.

11. The system of claim 10, wherein the portion of the mathematical sphere is positioned over the patient.

12. The system of claim 1, wherein the mathematical sphere is a physical or an imaginary sphere.

13. The system of claim 1, wherein the adjustment assembly allows adjustment in three linear dimensions: X, Y and Z.

14. The system of claim 1, wherein the spherical guide assembly and the adjustment assembly are integrated into an adjustment system allowing adjustment in X, Y, Z, $\Theta$, and $\Phi$ coordinates.

15. The system of claim 14, wherein the integrated adjustment system comprises a multi-axis articulated robotic arm and the system further comprises a landmarking assembly configured to register a position of the patient with respect to a coordinate system of the robotic arm.

16. The system of claim 1, further comprising:
 a control system including a computerized control and a display;
 the computerized control configured to receive acquired images of a selected target within the patient and adjust the positioning of at least one of the spherical guide assembly or the adjustment assembly so that the device guide is directed to the selected target; and
 the computerized control further configured to process the acquired images and present a processed image on the display that shows the target and a path to the target from the device guide.

\* \* \* \* \*